(12) United States Patent
Gozani et al.

(10) Patent No.: US 6,266,558 B1
(45) Date of Patent: Jul. 24, 2001

(54) APPARATUS AND METHOD FOR NERVE CONDUCTION MEASUREMENTS WITH AUTOMATIC SETTING OF STIMULUS INTENSITY

(75) Inventors: Shai N. Gozani, Brookline; Matthew A. Neimark; Christopher T. Turner, both of Somerville, all of MA (US)

(73) Assignee: NeuroMetrix, Inc., Cambridge, MA (US)

(*) Notice: Subject to any disclaimer, the term of this patent is extended or adjusted under 35 U.S.C. 154(b) by 0 days.

(21) Appl. No.: 09/204,032

(22) Filed: Dec. 1, 1998

(51) Int. Cl.⁷ ................................................ A61B 5/05
(52) U.S. Cl. ................................................ 600/547
(58) Field of Search ............................... 600/545, 546, 600/547, 587, 595

(56) References Cited

U.S. PATENT DOCUMENTS

| | | | |
|---|---|---|---|
| 3,886,931 | 6/1975 | Rodler | 128/2.1 |
| 4,807,643 | 2/1989 | Rosier | 128/741 |
| 5,080,099 | 1/1992 | Way et al. | 128/640 |
| 5,092,344 | 3/1992 | Lee | 128/741 |
| 5,131,401 | 7/1992 | Westenskow et al. | 128/741 |
| 5,143,081 | 9/1992 | Young et al. | 128/741 |
| 5,215,100 | 6/1993 | Spitz et al. | 128/741 |
| 5,284,154 | 2/1994 | Raymond et al. | 128/741 |
| 5,327,902 | 7/1994 | Lemmen | 128/734 |
| 5,333,618 | 8/1994 | Lekhtman et al. | 128/734 |

FOREIGN PATENT DOCUMENTS

| | | |
|---|---|---|
| 0 025 222 | 3/1981 | (EP) . |
| 91/16001 | 10/1991 | (WO) . |

OTHER PUBLICATIONS

Basmajian, M.D. et al. (1985), "Apparatus, Detection, and Recording Techniques", *Muscles Alive: Their Functions Revealed by Electromyography*, 5th Ed., Williams & Wilkin, Baltimore, pp. 19–64.

Carplay et al. (1997), "Coactivation of the ulnar nerve in motor tests for carpal tunnel syndrome", *Neurophysiol Clin.*, 27:309–313.

Chaudhry, M.D. (1997), "Technology Review: Nervepace Digital Electroneurometer", *AAEM Practice Topics in Electrodiagnostic Medicine*, 20:1200–1203.

Hodes (1965), "Low Threshold Associated With Slow Conduction Velocity", *Arch Neurol.*, 12:510–526.

*Primary Examiner*—Eric F. Winakur
*Assistant Examiner*—Pamela L Wingood
(74) *Attorney, Agent, or Firm*—Testa, Hurwitz & Thibeault, LLP (57) ABSTRACT

An apparatus and method of the invention provide for the measurement of sensory or motor nerve conduction parameters with automatic setting of stimulus intensity. An apparatus of the invention includes a stimulator for stimulating a nerve, a detector for detecting an evoked signal generated by the nerve or a muscle innervated by the nerve, and a controller for determining a stimulus intensity for use in conducting the measurements in response to the stimulation and evoked signal. Methods of the invention include stimulating a nerve, detecting an evoked signal generated by the nerve or by a muscle innervated by the nerve in response to the stimulation, and determining a stimulus intensity for use in conducting sensory or motor nerve conduction in response to the stimulation and evoked signal. In determining the stimulus intensity level, the nerve is stimulated at incrementally increasing stimulus intensities, and the respective evoked signals are detected. A parameter that quantifies the magnitude of each evoked signal is then determined, and the parameters of two consecutive evoked signals are compared until the parameter of one of the evoked signals is greater than a predetermined fraction of the parameter of an immediately succeeding evoked signal.

20 Claims, 5 Drawing Sheets

APPARATUS AND METHOD FOR NERVE CONDUCTION MEASUREMENTS WITH AUTOMATIC SETTING OF STIMULUS INTENSITY

FIELD OF THE INVENTION

The invention relates to an apparatus and method for measuring nerve conduction. More particularly, the invention relates to an apparatus and method for measuring nerve conduction which automatically sets the intensity of the stimulus used to conduct such measurements.

BACKGROUND OF THE INVENTION

Pathologies of the peripheral nerves and muscles are common clinical conditions. Carpal Tunnel Syndrome and diabetic neuropathy affect ten million individuals in the U.S. alone. Because they are so common, disease detection and early management are often the responsibility of general practitioners, such as primary care or family physicians, occupational physicians, and endocrinologist. These conditions are, however, difficult to diagnose and evaluate using only the clinical history and physical symptoms. The only objective way to investigate peripheral nerve disease is to measure nerve conduction parameters that quantify the transmission of neural signals between two points on a nerve or between a point on a nerve and a muscle innervated by that nerve. The gold standard approach is a formal nerve conduction study by a clinical neurologist. This diagnostic test, however, has a number of important disadvantages. First, it is time consuming and requires the services of a medical expert, such as a neurologist. Second, it is costly (e.g., typically $600–$1000). Third, it is generally not available in point-of-care environments where early detection and management would be expected to have the greatest potential impact on morbidity and medical costs.

As a result of these disadvantages, formal nerve conduction studies are used in a relatively restricted fashion. They are most often employed to confirm a diagnosis prior to a significant intervention, such as surgery. The potential clinical uses of nerve conduction information, however, go well beyond these limited applications into pointof-care testing for confirmation of clinical diagnoses, as well as into intensive monitoring to detect objective evidence of response to therapeutic interventions, such as pharmacological agents and physical therapy. Peripheral nerve diagnostics that are appropriate for point-of-care environments and that are easier-to-use and less-costly are, therefore, needed.

A nerve conduction measurement typically occurs by stimulating a nerve with a short electrical impulse and then measuring the evoked response along the same nerve at a second location for a sensory or mixed nerve measurement, or over a muscle innverated by the stimulated nerve for a motor nerve measurement. Nerve conduction is most often characterized by either the latency or the conduction velocity (determined from latency and distance between stimulation and detection sites) of the evoked response. The amplitude of evoked response is also used, but to a lesser degree. The accuracy and reliability of the nerve conduction measurement is dependent on a number of technical factors. One such factor is the magnitude of the electrical stimulus used to evoke the response. In particular, the intensity of the electrical stimulus must be set within a fairly narrow range. Identifying this range is complicated by the fact that its value varies from person to person, nerve to nerve, and even from time to time in a specific nerve in an individual.

The low end of the stimulus intensity range is defined by the fact that the nerve must be stimulated at an intensity for which additional increases in stimulus intensity do not lead to further increases in the amplitude of the evoked response. This response saturation effect results from the complete activation of all the large and fast conducting myelinated nerve fibers at a stimulus intensity called the maximal stimulus intensity. Further increases in intensity may activate smaller and slower conducting fibers, but these fibers do not contribute to the early portion of the nerve response from which most traditional nerve conduction parameters are measured. Because sub-maximal stimuli do not activate the fastest conducting nerve fibers, the measured nerve conduction parameters may appear artificially slow and small, thus mimicking nerve pathology. Stimulus intensities above this maximal stimulus intensity are called supramaximal. A "near maximal" stimulus intensity (e.g., within 10–20% of maximal) is sufficient for accurate and reliable latency and conduction velocity measurements. Amplitude measurements, however, still require use of a maximal or supramaximal stimulus intensity. Although the prior art reveals a number of attempts to simplify and automate the assessment of peripheral nerve physiology, it has failed to automate and optimize the process of establishing the ideal stimulus intensity for measuring the evoked response.

The stimulus intensity is limited at the high end by a number of measurement errors and patient issues that result from overly elevated stimulus intensities. First, high stimulus intensities may lead to a "virtual cathode" effect in which the apparent point of stimulation on the nerve shifts away from the actual site of the stimulating electrode. This may lead to an artificial increase in the nerve conduction velocity or, equivalently, a decrease in the nerve conduction latency. Second, high stimulus intensities may accidentally coactivate nerves that are anatomically adjacent to the intended nerve. This can severely distort the detected signals, particularly with motor nerve measurements in which the coactivated nerve innervates muscles in the vicinity of those innervated by the intended nerve. In extreme cases, the stimulus may directly activate muscles, thereby completely bypassing the peripheral nerve and yielding incorrect nerve conduction measurement values. Third, patient discomfort is generally related to stimulus intensity. Very high stimulus intensity can cause a significant amount of discomfort and even pain.

There remains, therefore, a need for apparatus and methods for assessing peripheral nerve physiology that are easy to use, rapid and automatic. Futhermore, in order to generate accurate and reliable nerve conduction parameters, these apparatus and methods must determine the lowest possible stimulus intensity that provides a maximal or near maximal evoked response. Such apparatus and methods are needed to provide more widespread early detection, prevention, and monitoring of peripheral nerve disease. The present invention addresses these needs.

SUMMARY OF THE INVENTION

The apparatus and method of the present invention provide for nerve conduction measurements with the automatic setting of stimulus intensity. An apparatus of the invention includes a stimulator for producing a stimulus and applying that stimulus to a nerve, and a detector for detecting an evoked signal generated by the nerve, or by a muscle innervated by the nerve, in response to the stimulation. In one embodiment, the nerve is a peripheral nerve. The stimulus generated by the stimulator includes, but is not limited to, an electrical, magnetic, or optical stimulus.

An apparatus of the invention further includes a controller for determining an operable stimulus intensity at which to measure sensory or motor nerve conduction and for directing the stimulator to stimulate the nerve at this operable stimulus intensity. The operable stimulus intensity may be the maximal stimulus intensity or the near maximal stimulus intensity. The controller may also determine the nerve conduction measurements and may generate a controller signal indicative of these measurements. A controller for use in the invention may be embodied as two separate controllers, which include both a main controller and a stimulator controller. When the invention is embodied with both a main controller and a stimulator controller, the main controller is for determining an operable stimulus intensity and for generating a stimulus signal, which is indicative of this operable stimulus intensity. The stimulator controller is in electrical communication with the main controller and is adapted for receiving the stimulus signal and for directing the stimulator to stimulate the nerve in response to this signal.

In other embodiments of the invention, an apparatus includes a display, which may be a liquid crystal display. In one embodiment, the display is adapted for receiving the controller signal from the controller and for indicating the nerve conduction measurements in response to that signal.

In another embodiment, an apparatus of the invention has an external interface for establishing communication between the controller and an external device. In one embodiment, the external device is a personal computer and is adapted for evaluating and indicating nerve conduction measurements in response to the response signal.

Finally, in another embodiment, an apparatus of the invention includes a converter for converting electrical stimuli produced by the stimulator into bioelectrical signals for stimulation of a nerve. A converter is also adapted for converting bioelectrical signals generated by a nerve into electrical signals for detection by the detector.

A method of the invention includes measuring sensory or motor nerve conduction by stimulating a nerve, which is preferably a peripheral nerve, detecting an evoked signal generated by that nerve or a muscle innervated by that nerve in response to the stimulation, determining an operable stimulus intensity in response to the stimulation and the evoked signal, and conducting sensory or motor nerve conduction measurements using the operable stimulus intensity so determined. The operable stimulus intensity may be either the maximal or the near maximal stimulus intensity for the nerve.

The step of determining the operable stimulus intensity includes three other steps: (1) the step of repeatedly stimulating the nerve at incrementally increasing stimulus intensities and detecting the evoked signals generated by the nerve at each of these stimulus intensities; (2) the step of determining a parameter which quantifies a magnitude of the evoked signal for each of the stimulus intensities; and (3) the step of comparing the parameters of two consecutive evoked signals until the parameter of one of the evoked signals is greater than a predetermined fraction of the parameter of an immediately succeeding evoked signal. The parameter quantifying the magnitude of the response may include a peak of a first derivative of the evoked signal, a peak of a second derivative of the evoked signal, and an amplitude of the evoked signal.

In one embodiment, the method of the invention includes the step of measuring a temperature of skin adjacent the nerve or muscle innervated by the nerve. These temperature measurements may then be used to adjust the parameters of the evoked signals relative to the temperature measurements. Finally, in another embodiment, the method of the invention includes the step of indicating the sensory or motor nerve conduction measurements.

Apparatus and method of the invention therefore provide for the measurement of sensory and motor nerve conduction with automatic setting of maximal or near maximal stimulus intensities. The invention therefore provides for sensory or motor nerve conduction measurements without the use of a medical expert, without the high cost of traditional measurements, and without significant discomfort to the patient.

DESCRIPTION OF THE DRAWINGS

Apparatus and methods of the invention will be understood further upon consideration of the following drawings, description, and claims.

DETAILED DESCRIPTION OF THE INVENTION

An apparatus and method are provided for automatically determining the intensity of a stimulus to be applied to a peripheral nerve in the course of performing a nerve conduction measurement. In various embodiments, the stimulus is an electrical, magnetic or optical stimulus, but is preferably an electrical stimulus. Because the invention utilizes a model of the peripheral nerve stimulus-response relationship, it can automatically and optimally identify an operable stimulus intensity. An operable stimulus intensity includes a stimulus intensity at which sensory or motor nerve conduction measurements may be taken without significant discomfort to the patient/user. An operable stimulus intensity includes a near maximal stimulus intensity and a maximal stimulus intensity. As previously described, a maximal stimulus intensity is a stimulus intensity above which increases in stimulus intensity do not lead to further increases in the amplitude of the evoked response. The invention provides apparatus and methods to determine and control the stimulus intensity so as to ensure that the final stimulus intensity is greater than a fraction of the maximum obtainable response of the stimulated nerve. This final stimulus intensity is preferably within about 10% to about 20% of the maximal stimulus intensity and is called the near maximal stimulus intensity. Thus, the present invention has the substantial advantage that it will provide consistent and repeatable nerve conduction measurements that may be determined automatically and rapidly without involvement of the operator. Furthermore, because the stimulus intensity is set automatically, the method will exhibit improved reliability over the prior art.

The present invention has the further advantage that the automatically determined stimulus intensity is the smallest intensity that provides a near maximal response amplitude. This advantage reduces the probability of a number of technical errors that can decrease the accuracy and reliability of nerve conduction measurements. These errors include the "virtual cathode" effect, direct muscle stimulation and coactivation of anatomically adjacent nerves. This advantage also reduces patient discomfort associated with electrical stimulation.

Figure 1:
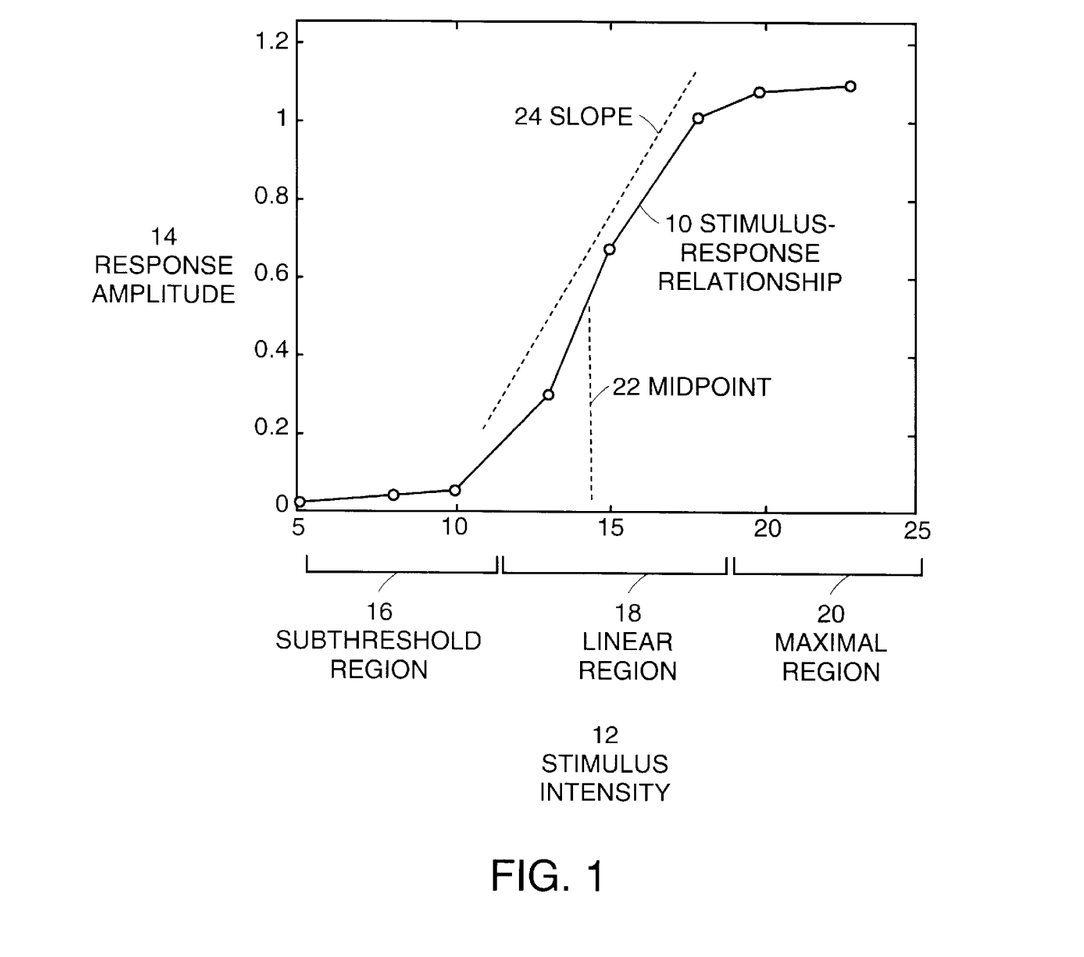
FIG. 1 shows the non-linear relationship between the stimulus intensity and the amplitude of the evoked response in a peripheral nerve.

Referring to FIG. 1, peripheral nerves exhibit a non-linear relationship, as shown by stimulus-response curve 10, between stimulus intensity 12 and the amplitude of the evoked response 14. This particular stimulus-response curve 10 was obtained by stimulating the median nerve at the wrist with constant current pulses and detecting the evoked myoelectrical response from the thenar muscles. Thus, FIG. 1 shows the stimulus-response curve 10 for the median motor nerve. The horizontal axis 12 indicates the intensity of the electrical stimulus in milliamps, and the vertical axis 14 shows the peak amplitude in millivolts of the evoked myoelectrical response.

At very low stimulus intensities 16, the stimulus is below the threshold for activation of the fast conducting myelinated nerve fibers, and there is, therefore, little, if any, muscle response. Consequently, at these levels the stimulus-response curve 10 changes little with increasing intensity and is essentially flat. At intermediate intensities 18, the stimulus progressively exceeds the threshold for activation of increasing numbers of fast conducting myelinated nerve fibers. This causes the stimulus-response curve 10 to change sharply and in a nearly linear fashion with intensity. Finally, at high stimulus intensity levels 20, the stimulus-response curve 10 again changes little with increasing intensity, because essentially all the fast conducting myelinated nerve fibers are above threshold and are contributing to the detected muscle response. As previously described, this latter stimulus intensity region is called the maximal or supramaximal region, because the response is at its maximal level despite continued increases in stimulus intensity. The stimulus-response relationship 10 demonstrated in FIG. 1 is characteristic of all peripheral nerves, but the stimulus intensity defining the midpoint 22 of the curve and the slope 24 of the curve varies from subject to subject, nerve to nerve, and even from time to time in the same nerve and subject.

As described previously, it is advantageous to automate the process of finding the maximal stimulus intensity. In the present invention this is accomplished by utilizing knowledge of the physiology of the nerve, particularly the non-linear stimulus-response relationship 10, as shown in FIG. 1.

Figure 2:
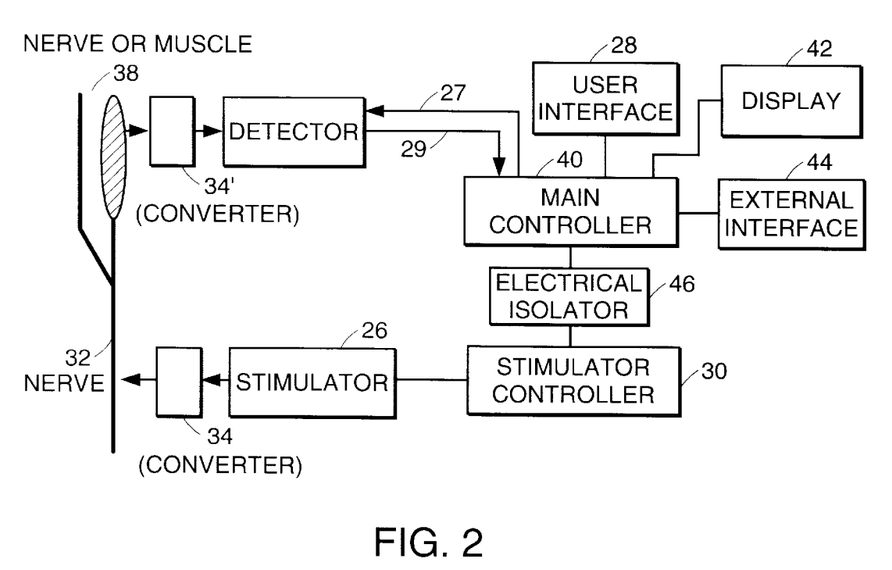
FIG. 2 is a block diagram of an embodiment of an apparatus of the invention.

An illustrative block diagram of an apparatus of the invention is shown in FIG. 2. Stimulator 26 generates a stimulus, and preferably generates an electrical stimulus. Unlike the prior art, the parameters of the stimuli are not determined by user actuated controls 28, but rather by control signals from stimulator controller 30, which is in electrical communication with stimulator 26. In a preferred embodiment, stimulator controller 30 is a single, integrated, low-cost embedded microcontroller. In a preferred embodiment, the stimuli are electrical stimuli of constant current pulses with amplitude and duration controlled by digital signals from stimulator controller 30. Other embodiments include electrical stimuli of constant voltage pulses or arbitrary waveforms. Stimulator 26 delivers stimuli to a peripheral nerve 32 through converter 34. Converter 34 includes a bioelectrical interface or any other means to convert electronic signals into bioelectrical signals that pass through the skin surface. In a preferred embodiment, converter 34 is a conventional silver/silver-chloride biomedical electrode located on the skin surface and is in electrical communication with stimulator 26.

Detector 36 detects biopotentials generated by a nerve or muscle 38. In a preferred embodiment, detector 36 is a high input impedance, high common mode rejection instrumentation amplifier followed by signal conditioning circuitry that amplify and filter biopotentials prior to digitization of the signals by main controller 40. Detector 36 also performs variable gain amplification of the detected biopotentials. Gain control is established by digital signals 27 from main controller 40. Detector 36 detects the biopotentials through a converter 34'. Converter 34' converts bioelectrical signals at the skin surface into electronic signals. In a preferred embodiment, converter 34' is a conventional silver/silver-chloride biomedical electrode located on the skin surface and in electrical communication with detector 36.

The output of detector 36 is in electrical communication 29 with the input of main controller 40, which digitizes, processes, and stores the waveforms acquired by the detector 36. In one embodiment, main controller 40 analyzes the waveforms. The parameters extracted from the waveforms include, but are not limited to, the peak amplitude of the waveform, the delay between the onset of the stimulus and the onset of the waveform, and the delay between the onset of the stimulus and the peak of the waveform. In one embodiment, main controller 40 also calculates and processes first and second derivatives of detected waveforms prior to extraction of the above-listed parameters. In one embodiment of the invention, the apparatus also includes a temperature sensor for measuring the temperature of the surface of the skin that is above the nerve or muscle innervated by the nerve from which conduction measurements are being taken. In this embodiment, the temperature sensor is in electrical communication with main controller 40, which adjusts the parameters described above in response to the skin temperature.

Main controller 40 is preferably embodied as a single, integrated, low-cost embedded microcontroller. In other embodiments, main controller 40 has multiple components, such as, for example, a microprocessor and external components that perform analog-to-digital conversion and other necessary functions.

User interface 28 allows the operator to interact with the apparatus. User interface 28 is in electrical communication with main controller 40. In a preferred embodiment, user interface 28 includes momentary pushbutton switches. Display 42 is also in electrical communication with main controller 40 and provides visual feedback to the operator regarding the results of the nerve conduction measurement or provides messages should measurement errors occur. In a preferred embodiment, display 42 is a liquid crystal display. Finally, external interface 44 communicates with external devices, such as a personal computer or a modem, for example. The external interface 44 is preferably in electrical communication with main controller 40 and is preferably embodied as an infra-red serial communication link. The external interface 44 is used to couple with external devices for evaluating nerve conduction parameters and for indicating those parameters to a user.

Main controller 40 is in electrical communication with stimulator controller 30 through isolator 46. In a preferred embodiment, isolator 46 is an optical isolator. Main controller 40 communicates with stimulator controller 30 in a master/slave relationship. Although the preferred embodiment utilizes a main controller 40 and a stimulator controller 30, other embodiments in which only a single controller is used have been contemplated.

Figure 3:
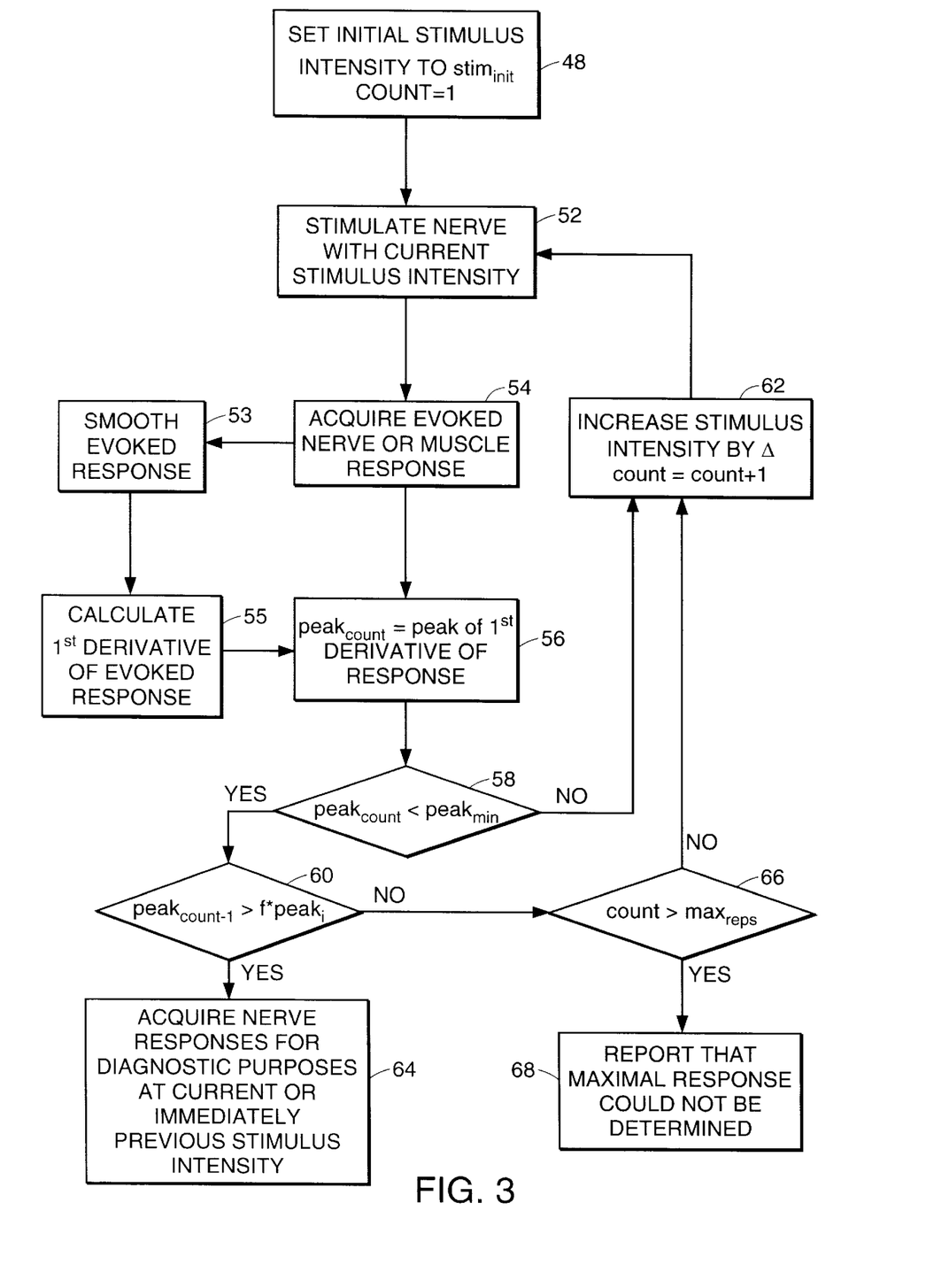
FIG. 3 is a flow chart of a method for establishing a maximal or near maximal stimulus intensity.

In accordance with a preferred embodiment of the present invention, FIG. 3 shows an illustrative method for determining the maximal stimulus intensity automatically. The method commences in process step 48 by setting the stimulus intensity to a predetermined initial level, $stim_{init}$. This initial stimulus intensity is empirically chosen to be below the expected threshold for evoking a detectable response in the majority of individuals. The stimulus intensity is preferably within the range of about 0 mA to about 10 mA, and is more preferably within the range of about 2 mA to about 6 mA. For example, when stimulating the median nerve at the wrist and detecting the evoked myoelectrical response from the thenar muscles, $stim_{init}$ is set at about 5 mA for about 200 μs. In addition, as shown in FIG. 3, a stimulus counter, count, is initialized to one in process step 48.

In process step 52, the target nerve is stimulated with an electrical pulse having the currently established intensity (e.g., $stim_{init}$ if a first stimulus). Immediately thereafter, in process step 54, the bioelectrical response evoked by said stimulus is detected. Subsequently, in process step 56, a parameter ($peak_{count}$) quantifying the magnitude of the response is automatically determined. In the illustrative method, the peak of the first derivative of the evoked response is used for the parameter $peak_{count}$. In other embodiments, other parameters, such as the peak of the second derivative or the amplitude of the evoked response or the amplitude of the evoked response, is used in process step 56. Furthermore, in other embodiments, parameters obtained from averaging responses evoked by multiple stimuli may be used in process step 56.

In a preferred embodiment, the peak of the first derivative is obtained in process step 53 by first smoothing the evoked response, such as, for example, by convolving it with a smoothing function. Subsequently, the first derivative is calculated in process step 55 by estimating the instantaneous slope for each data point in the detected evoked response. The smoothing and first derivative operations can be combined and applied to small sections of the response curve and the values discarded if they do not indicate the presence of a peak in the first derivative. To avoid detection of spurious signals, such as those related to a stimulus artifact, the peak of the first derivative is evaluated within a defined time window in process step 56. This time window is defined as occurring within two time limits, $t_1$ and $t_2$. In a preferred embodiment, the lower time limit ($t_1$) is predetermined and reflects the amount of time required for artifacts associated with the stimulus to decay to an amplitude that is significantly less than the amplitude of the actual evoked response signal. The lower time limit ($t_1$) is preferably within the range of about 1.0 ms to about 2.5 ms. The lower time limit ($t_1$) is more preferably about 2 ms. Other lower time limits may, however, be used. In addition, it is possible to dynamically establish the lower time limit ($t_1$) by analyzing the amplitude decay of the stimulus associated artifact. In a preferred embodiment, the upper time limit ($t_2$) is predetermined and must be larger than the longest delay expected before the onset of the evoked response. Both the upper ($t_2$) and lower ($t_1$) time limits are determined empirically through routine testing commonly know to those of ordinary skill in the art. The actual value of the upper time limit ($t_2$) depends on the specific peripheral nerve being tested as well as the distance between the stimulation and detection sites.

Use of the peak of the first derivative to track changes in the amplitude of the response is advantageous, because the first derivative is considerably less affected by the stimulus artifact and other sources of baseline variation than is the actual evoked response. Furthermore, since the first derivative is a linear function of the actual response, the peak of the first derivative increases with the peak of the evoked response itself. Nevertheless, embodiments in which the peak of the response is used have been contemplated, as well as embodiments in which the peak of the second derivative or amplitude of the evoked response is used.

In process step 56, the first derivative of the response signal is measured with the assumption that the signal represents a viable evoked myoelectrical response. Referring again to FIG. 1, if the stimulus intensity is in the subthreshold region 16 of the stimulus-response curve, such a signal should not occur. Thus it is essential to validate that an actual nerve or muscle response was in fact obtained, which would imply that the stimulus intensity is in either the linear 18 or maximal 20 region of the stimulus-response curve.

In a preferred embodiment, this is accomplished in process step 58, by comparing the peak of the first derivative of the evoked response ($peak_{count}$) against a predetermined threshold $peak_{min}$) If the first derivative peak exceeds the threshold, the method assumes that a viable evoked response was obtained and continues to process step 60. On the other hand, if the first derivative peak falls below the threshold, the method proceeds to process step 62.

This predetermined threshold is obtained by processing biopotential signals detected by detector 36 of FIG. 2 in the absence of stimulation by stimulator 26 of FIG. 2. Under these conditions, the acquired signal represents noise sources only. The distribution of the first derivative of this "noise only signal" is determined. Based on this distribution, a threshold is chosen (i e., $peak_{min}$) that will have a very low probability of being exceeded by a signal consisting only of noise. In a preferred embodiment, a threshold that is three standard deviations above the mean is chosen (i.e., less than 2.5% of signals containing only noise will exceed this value). Thus, an evoked response signal with a peak first derivative that exceeds this threshold is expected to represent an actual evoked response signal rather than noise.

There are other methods of accomplishing the objective of process step 58 (i.e., of determining that the detected response represents a viable myoelectrical signal). In one such additional embodiment, a neural network that has been trained, such as by back propagation, to differentiate noise or stimulus artifacts from actual myoelectrical signals is applied to the detected signals. In another embodiment, more elaborate waveform features than the peak of the first derivative are utilized. For example, the difference between the positive and negative first derivative peaks has been contemplated. In yet another embodiment, matched filters that are tuned to the power spectral characteristics of evoked myoelectrical signals are utilized.

In process step 60 the amplitudes of the responses ($peak_{count-1}$ and $peak_{count}$) evoked by the last two stimulus intensities are compared. If the amplitude of the response evoked by the previous stimulus ($peak_{count-1}$) is larger than a predetermined fraction ($f$) of the amplitude of the response evoked by the current stimulus ($peak_{count}$), then according to the non-linear stimulus-response relationship 10 of FIG. 1, the stimulus intensity must be in the maximal region 20. The method for determining ($f$) for a preferred embodiment of the invention is outlined below. If the predetermined fraction ($f$) is less than 1, the method has identified a near maximal stimulus intensity. If the predetermined fraction is greater or equal to 1, the method has identified a maximal or supramaximal stimulus intensity. The predetermined fraction ($f$) is preferably within the range of about 0.7 to about 1.1 and is more preferably within the range of about 0.8 to about 0.95. Measurements of the amplitudes may be affected by skin temperature, so another embodiment of the invention includes the step of measuring skin temperature adjacent the nerve or muscle innervated by the nerve and adjusting the amplitude in response to that temperature. Upon finding the maximal or near maximal stimulus intensity, the method proceeds to process step 64, where nerve conduction measurements are made.

In a preferred embodiment, the near maximal value of the fraction is determined empirically by analyzing stimulus-response curves obtained from a broad population of individuals in order to determine which fraction clearly identifies an evoked response that is consistently within 85% of the maximal possible response. (The 85% level was shown to be near maximal in Hodes, et al., "Low Threshold Associated with Slow Conduction Velocity," 12 Arch. Neurol. 510–526 (1965).) This was accomplished by setting the value off to 1.0, which forced the algorithm to achieve a maximal or supramaximal level. The resulting stimulus-response curves were then analyzed to determine which value off would have yielded a response within 85% of the maximal response. Based on these experiments, it was determined that a value of $f=0.90$ would consistently yield such an evoked response. In the preferred embodiment, this value off was therefore chosen.

If the inequality tested in process step 60 is false, the current stimulus intensity is not in the maximal region of the stimulus-response curve 10 of FIG. 1. The method of FIG. 3 then proceeds to process step 66. In this step, the total number of stimuli that have been delivered is compared against a predetermined maximum number of stimuli ($max_{reps}$). The value of $max_{reps}$ is preferably less than about 30. If the number of stimuli exceeds this predetermined limit, the method proceeds to process step 68. If the number of stimuli does not exceed the predetermined limit, however, the method proceeds to process step 62 where the stimulus intensity is increased. In a preferred embodiment, the stimulus intensity is increased by a predetermined amount ($\Delta$) that is based on empirical experience. This amount ($\Delta$) is preferably within the range of about 0 mA to about 20 mA and is more preferably within the range of about 0 mA to about 2.5 mA. This amount ($\Delta$) is determined empirically through routine testing commonly known to those of ordinary skill in the art. Other embodiments have, however, been contemplated in which the stimulus is increased by a variable amount, such as, for example, in relation to the difference in the amplitude of the responses ($peak_{count} - peak_{count-1}$) evoked by the last two stimuli. In yet another embodiment, the stimulus intensity is increased according to a lookup table stored in either main controller 40 or stimulator controller 30 of FIG. 2. After increasing the stimulus intensity, the method returns to process step 52.

Process step 68 is reached if the inequality tested in process step 66 is true. In this case, a maximal or near maximal stimulus intensity could not be determined within the redetermined number of stimuli ($max_{reps}$). Since nerve conduction measurements require a maximal or near maximal stimulus intensity, the method reports that such an intensity could not be achieved and does not proceed to acquire further nerve responses for diagnostic purposes.

Process step 64 is reached if the inequality tested in process step 60 is true. As described above, the implication of satisfying this inequality is that the stimulus intensity must be in the maximal region 20 of the stimulus-response relationship 10 of FIG. 1. In step 64, the nerve is therefore stimulated with either the current or immediately preceding stimulus intensity, since both reside within the maximal region 20 of the stimulusresponse relationship 10, as shown in FIG. 1. A preferred embodiment may use the preceding stimulus intensity, because it is more moderate and, thus, less likely to cause discomfort to the patient. The responses evoked by stimuli with the given stimulus intensity are then analyzed, and nerve conduction parameters are extracted and utilized for diagnostic purposes.

Figure 4A:
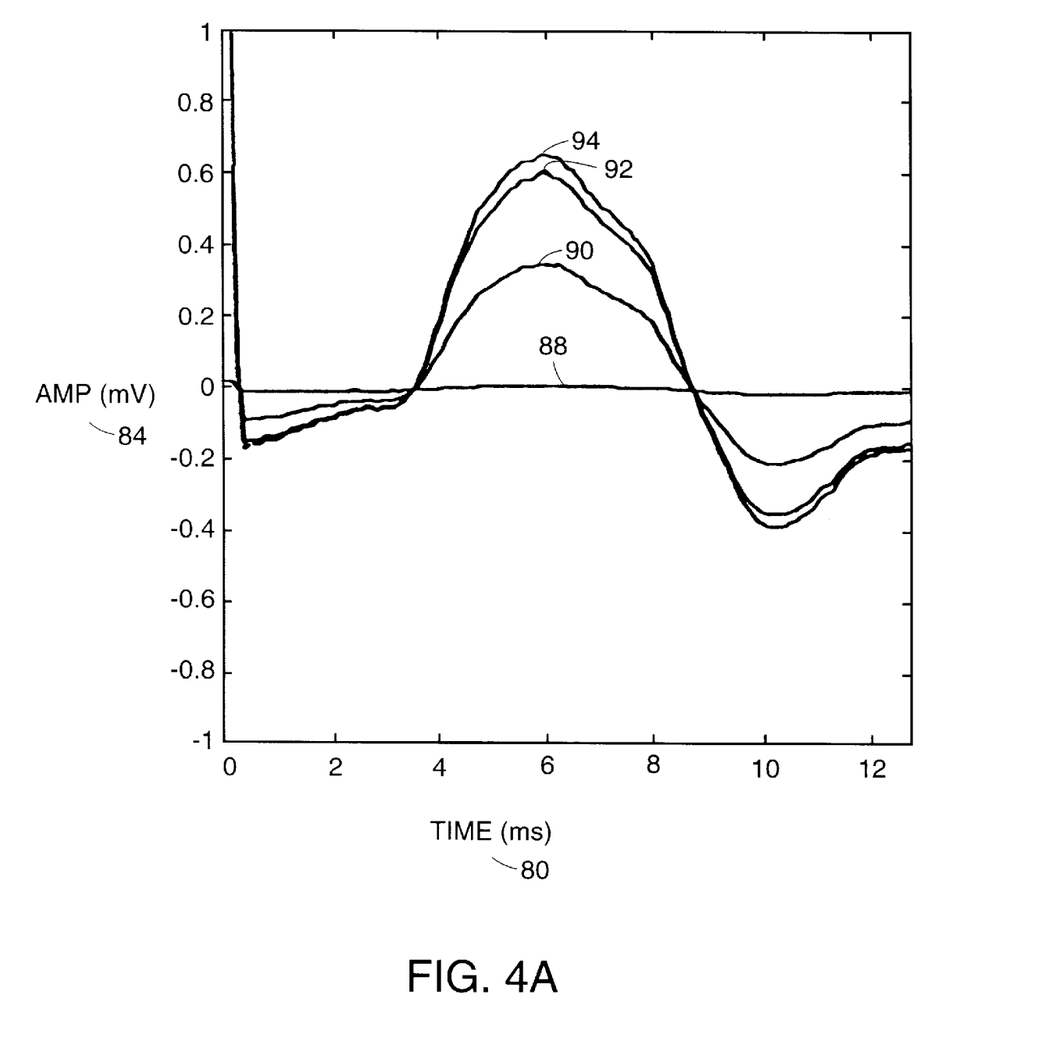
FIGS. 4A and 4B shows a series of responses evoked by a median nerve that is stimulated using an apparatus and method of the invention.
Figure 4B:
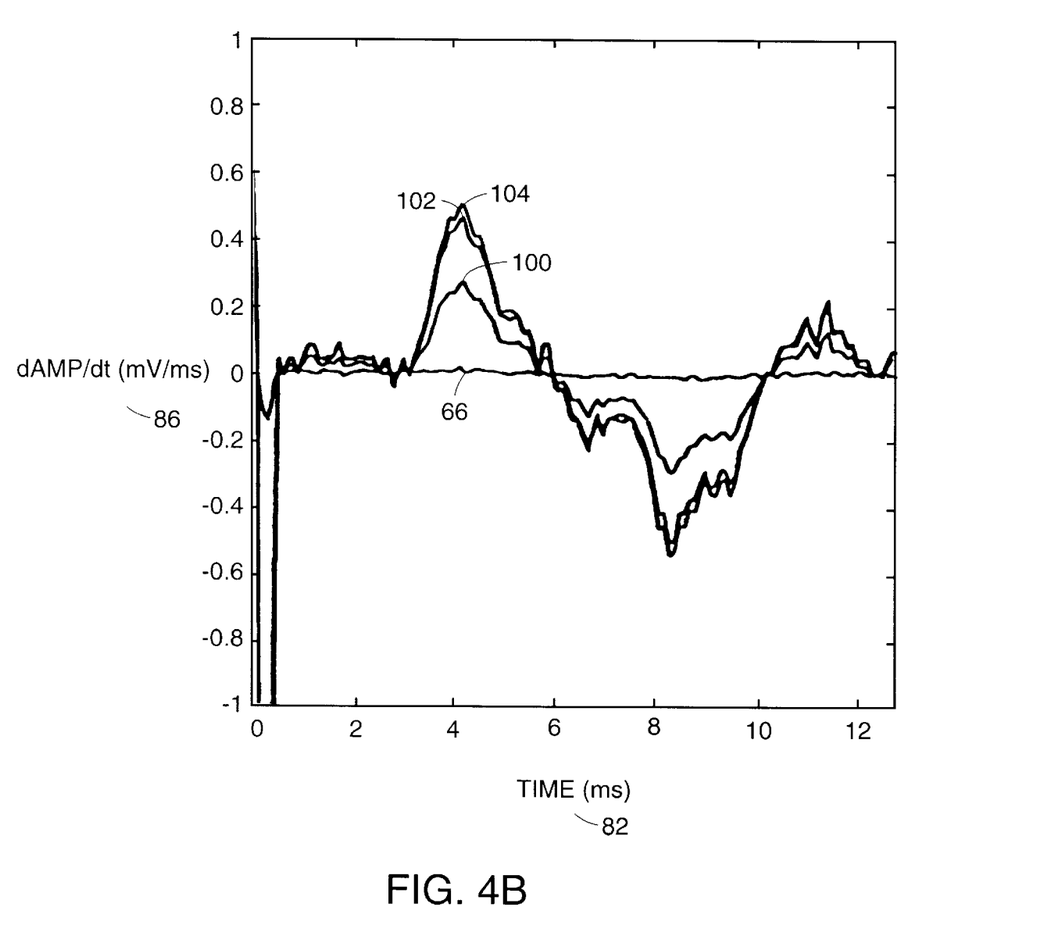

FIGS. 4A and 4B show several bioelectrical responses evoked by a preferred embodiment of the invention in the course of automatically determining a near maximal stimulus intensity. These responses were obtained by stimulating the median nerve at the wrist and detecting the evoked myoelectrical response from the thenar muscles. FIG. 4A shows the evoked bioelectrical response as a function of time, and FIG. 4B shows the first derivative of the evoked response as a function of time. In both FIGS. 4A and 4B, the horizontal axis 80, 82 shows the time in milliseconds after the onset of the stimulus. In FIG. 4A, the vertical axis 84 shows the amplitude, in millivolts, of the response. In FIG. 4B, the vertical axis 86 shows the rate of change in the amplitude as a function of time.

The smallest response 88 was evoked with the initial stimulus intensity established in step 48 of the preferred method of FIG. 3. The remaining responses 90, 92, and 94 were evoked by stimuli with progressively higher intensities resulting from increases to the stimulus intensity in step 62 of the preferred method of FIG. 3. As can be seen from FIG. 4B, the peaks of the first derivatives of the responses 98, 100, 102 and 104 increase in parallel with the peaks of the responses 88, 90, 92, and 94.

The largest response 94 satisfied the branch condition in step 60 of the preferred method of FIG. 3. The peak of the first derivative of this response 104 was 0.502, while the peak of the first derivative of the response 102 evoked at the previous stimulus intensity was 0.457. The ratio (previous response over current response) between these two peaks was 0.91, which was larger than the preferred cutoff for the median motor nerve of 0.90, as described above. Thus, according to step 74 of the preferred method, the stimulus intensity that evoked response 94 or 96 represented a near maximal stimulus intensity that was suitable for measuring nerve responses of the median motor nerve for diagnostic purposes.

While the present invention has been described in terms of certain exemplary preferred embodiments, it will be readily understood and appreciated by one of ordinary skill in the art that it is not so limited, and that many additions, deletions, and modifications to the preferred embodiments may be made within the scope of the invention as hereinafter claimed. Accordingly, the scope of the invention is limited only by the scope of the appended claims.

What is claimed is:

1. An apparatus for measuring sensory and motor nerve conduction with automatic setting of stimulus intensity, comprising:

(a) a stimulator capable of producing a stimulus and for applying said stimulus to a nerve;

(b) a detector capable of detecting at least two sequential evoked signals from said nerve or from a muscle innervated by said nerve in response to said stimulus; and (c) a controller for automatically determining an operable stimulus intensity at which to measure nerve conduction in response to said stimulus and said evoked signal and for directing said stimulator to stimulate said nerve at said operable stimulus intensity, said controller comprising a comparator for comparing said at least two sequential evoked signals until one evoked signal is greater than a predetermined faction of an immediately succeeding evoked signal, whereby nerve conduction is then measured using said operable stimulus intensity.

2. The apparatus of claim 1, wherein said operable stimulus intensity is selected from the group consisting of a maximal stimulus intensity and a near maximal stimulus intensity.

3. The apparatus of claim 1, wherein said controller is further for determining a nerve conduction measurement in response to said evoked signal and for producing a controller signal indicative of said nerve conduction measurement.

4. The apparatus of claim 3, further comprising a display in electrical communication with said controller and for receiving said controller signal and for indicating said sensory or motor nerve conduction measurements in response to said controller signal.

5. The apparatus of claim 4, wherein said display is a liquid crystal display.

6. The apparatus of claim 1, wherein said stimulus is selected from the group consisting of an electrical stimulus, a magnetic stimulus, and an optical stimulus.

7. The apparatus of claim 1, further comprising an external interface for establishing communication between said controller and an external device, whereby said external device is adapted for evaluating and for indicating said nerve conduction measurements in response to said evoked signal.

8. The apparatus of claim 1, further comprising a converter for converting electrical stimuli produced by said stimulator into bioelectrical signals for stimulation of a nerve.

9. The apparatus of claim 8, wherein said converter is further for converting bioelectrical signals generated by a nerve into electrical signals for detection by said detector.

10. The apparatus of claim 1, wherein said controller comprises a main controller and a stimulator controller.

11. The apparatus of claim 10, wherein said main controller is for determining said operable stimulus intensity and for generating a stimulus signal indicative of said operable stimulus intensity.

12. The apparatus of claim 11, wherein said stimulator controller is in electrical communication with said main controller and is for receiving said stimulus signal and for directing said stimulator to stimulate said nerve at said operable stimulus intensity.

13. The apparatus of claim 1, further comprising a temperature sensor for measuring the temperature of skin adjacent said nerve or muscle innervated by said nerve.

14. The apparatus of claim 13, wherein said controller is further for adjusting said sensory or motor nerve conduction measurement in response to said measured temperature.

15. The method of claim 14, wherein said operable stimulus intensity is selected from the group consisting of a maximal stimulus intensity and a near maximal stimulus intensity.

16. A method for measuring sensory or motor nerve conduction with automatic setting of stimulus intensity, comprising the steps of:
(a) stimulating a nerve;
(b) detecting an evoked signal generated by said nerve or by a muscle innervated by said nerve in response to said stimulation;
(c) automatically determining an operable stimulus intensity in response to said stimulation and said evoked signal;
(d) conducting said sensory or motor nerve conduction measurements using said operable stimulus intensity;
(e) repeating steps (a) and (b) at incrementally increasing stimulus intensities;
(f) determining a parameter which quantifies a magnitude of said response signal; and
(g) comparing said parameters of two sequential evoked signals until said parameter of one of said evoked signals is greater than a predetermined fraction of said parameter of an immediately succeeding evoked signal.

17. The method of claim 16, wherein said parameter is selected from the group consisting of a peak of a first derivative of said evoked signal, a peak of a second derivative of said evoked signal, and an amplitude of said evoked signal.

18. The method of claim 16, further comprising the step of measuring a temperature of skin adjacent said nerve or muscle innervated by said nerve.

19. The method of claim 18, further comprising the step of adjusting said parameter in response to said measured temperature.

20. The method of claim 16, further comprising the step of indicating said sensory or motor nerve conduction measurements.

\* \* \* \* \*